(12) United States Patent
Schwarz (10) Patent No.: US 7,540,473 B2
(45) Date of Patent: Jun. 2, 2009

(54) DISPENSING SYSTEM FOR A VOLATILE LIQUID

(75) Inventor: Ralph Schwarz, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 589 days.

(21) Appl. No.: 11/341,046

(22) Filed: Jan. 25, 2006

(65) Prior Publication Data

US 2006/0170119 A1    Aug. 3, 2006

Related U.S. Application Data

(63) Continuation-in-part of application No. 10/608,717, filed on Jun. 27, 2003, now abandoned, and a continuation-in-part of application No. 10/394,621, filed on Mar. 21, 2003, now Pat. No. 7,032,831, and a continuation-in-part of application No. 10/607,702, filed on Jun. 27, 2003, now abandoned.

(51) Int. Cl.
*B01F 3/04* (2006.01)

(52) U.S. Cl. .................. 261/30; 261/104; 261/107; 261/DIG. 88

(58) Field of Classification Search .................. 261/26, 261/30, 104, 94, 99, DIG. 88; 422/124
See application file for complete search history.

(56) References Cited

U.S. PATENT DOCUMENTS

| | | | |
|---|---|---|---|
| 1,129,897 A | 3/1915 | Owen, Jr. | |
| 1,911,871 A | 5/1933 | Anderson | |
| 2,435,811 A | 2/1948 | Waters | |
| 2,472,992 A | 6/1949 | Szekely | |
| 2,557,501 A | 6/1951 | Fusay et al. | |
| 2,668,993 A | 2/1954 | Bair | |
| 2,754,554 A | 7/1956 | Mills | 422/121 |
| 2,764,789 A | 10/1956 | Zelenka | |
| 2,828,953 A | 4/1958 | Hartmann | |
| 2,867,866 A | 1/1959 | Steele | 422/124 |
| 2,897,671 A | 8/1959 | Phelan et al. | |
| 2,931,880 A | 4/1960 | Yaffe | |
| 3,080,624 A | 3/1963 | Weber, III | |
| 3,522,935 A | 8/1970 | Lewis | |

(Continued)

FOREIGN PATENT DOCUMENTS

AU    664685    11/1995

(Continued)

OTHER PUBLICATIONS

Office Action for U.S. Appl. No. 11/289,471 dated Apr. 26, 2006

(Continued)

*Primary Examiner*—Robert A Hopkins (57) ABSTRACT

A dispensing system for a volatile liquid, comprises a motorized fan adapted to generate an air stream and a capillary member having a body, in which a portion of the body is positioned within the air stream when the fan is activated. The portion of the body of the capillary member is impervious to passage of the air stream through the body in a direction of the air stream. The portion of the body is positioned in the air stream such that the air stream passes unobstructed over opposing surfaces of the capillary member aligned generally transverse to the direction of the air stream.

19 Claims, 3 Drawing Sheets

U.S. PATENT DOCUMENTS

| | | | |
|---|---|---|---|
| 3,550,853 A | 12/1970 | Gray | |
| 3,587,968 A | 6/1971 | Balland et al. | |
| 3,633,881 A | 1/1972 | Yurdin et al. | |
| 3,748,464 A | 7/1973 | Andeweg | |
| 3,749,904 A | 7/1973 | Graff | |
| 3,761,702 A | 9/1973 | Andeweg | |
| 3,790,081 A | 2/1974 | Thornton | |
| 3,804,592 A | 4/1974 | Garbe | |
| 3,890,085 A | 6/1975 | Andeweg | |
| 3,903,022 A | 9/1975 | Ohara et al. | |
| 3,923,458 A | 12/1975 | Moran | |
| 3,948,445 A | 4/1976 | Andeweg | |
| 3,979,179 A | 9/1976 | Teng | |
| 3,990,848 A | 11/1976 | Corris | |
| 3,993,444 A | 11/1976 | Brown | |
| 4,035,451 A | 7/1977 | Tringali | |
| 4,059,422 A | 11/1977 | Steiner | |
| 4,166,087 A | 8/1979 | Cline | |
| 4,173,604 A | 11/1979 | Long | |
| 4,173,605 A | 11/1979 | Long | |
| 4,276,236 A | 6/1981 | Sullivan | |
| 4,294,778 A | 10/1981 | DeLuca | |
| 4,301,095 A | 11/1981 | Mettler et al. | |
| 4,323,193 A | 4/1982 | Compton | |
| 4,346,059 A | 8/1982 | Spector | |
| 4,370,300 A | 1/1983 | Mori et al. | |
| 4,383,951 A | 5/1983 | Palson | |
| 4,387,849 A | 6/1983 | Van Loveren et al. | |
| 4,396,557 A | 8/1983 | DeLuca | |
| 4,419,326 A | 12/1983 | Santini | |
| 4,432,938 A | 2/1984 | Meetze, Jr. | |
| 4,445,641 A | 5/1984 | Baker et al. | |
| 4,477,414 A | 10/1984 | Muramoto et al. | |
| 4,493,011 A | 1/1985 | Spector | |
| 4,605,165 A | 8/1986 | Van Loveren et al. | |
| 4,614,211 A | 9/1986 | Mettler | |
| 4,614,299 A | 9/1986 | Van Loveren et al. | |
| 4,621,768 A | 11/1986 | Lhoste et al. | |
| 4,660,764 A | 4/1987 | Joyaux et al. | |
| 4,666,638 A | 5/1987 | Baker | |
| 4,695,435 A | 9/1987 | Spector | |
| 4,707,338 A | 11/1987 | Spector | |
| 4,739,928 A | 4/1988 | O'Neil | |
| 4,743,406 A | 5/1988 | Steiner et al. | |
| 4,774,032 A | 9/1988 | Coates et al. | |
| 4,857,240 A | 8/1989 | Kearnes et al. | |
| 4,866,580 A | 9/1989 | Blackerby | |
| 4,913,350 A | 4/1990 | Purzycki | |
| 4,928,881 A | 5/1990 | Barlics et al. | |
| 4,931,224 A | 6/1990 | Holzner, Sr. | |
| 4,968,487 A | 11/1990 | Yamamoto et al. | |
| 5,000,383 A | 3/1991 | van der Heijden | |
| 5,014,913 A | 5/1991 | Hoyt et al. | |
| RE33,864 E | 3/1992 | Steiner | |
| 5,094,025 A | 3/1992 | Daniels | |
| 5,095,647 A | 3/1992 | Zobele et al. | |
| 5,114,625 A | 5/1992 | Gibson | |
| 5,126,078 A | 6/1992 | Steiner et al. | |
| 5,133,042 A | 7/1992 | Pelonis | |
| 5,217,696 A | 6/1993 | Wolverton et al. | |
| 5,222,186 A | 6/1993 | Schimanski et al. | 385/122 |
| 5,223,182 A | 6/1993 | Steiner et al. | |
| 5,324,490 A | 6/1994 | Van Vlahakis et al. | |
| 5,334,162 A | 8/1994 | Harris | |
| 5,342,584 A | 8/1994 | Fritz et al. | |
| 5,370,829 A | 12/1994 | Kunze | |
| 5,376,338 A | 12/1994 | Zlotnik | |
| 5,402,517 A | 3/1995 | Gillett et al. | |
| 5,431,885 A | 7/1995 | Zlotnik et al. | |
| 5,437,410 A | 8/1995 | Babasade | |
| 5,484,086 A | 1/1996 | Pu | |
| 5,497,942 A | 3/1996 | Zingle et al. | |
| 5,547,616 A | 8/1996 | Dancs et al. | |
| 5,591,395 A | 1/1997 | Schroeder et al. | |
| 5,613,625 A | 3/1997 | Specht | |
| 5,647,053 A | 7/1997 | Schroeder et al. | |
| 5,651,942 A | 7/1997 | Christensen | |
| 5,662,835 A | 9/1997 | Collingwood | |
| D386,974 S | 12/1997 | Wefler | |
| D393,063 S | 3/1998 | Wefler | |
| 5,725,152 A | 3/1998 | Akyu | |
| 5,800,741 A | 9/1998 | Glenn et al. | |
| 5,802,865 A | 9/1998 | Strauss | |
| 5,876,678 A | 3/1999 | Harrell et al. | |
| 5,891,400 A | 4/1999 | Ansari et al. | |
| 5,909,845 A | 6/1999 | Greatbatch | |
| 5,919,423 A | 7/1999 | Requejo et al. | |
| 5,932,147 A | 8/1999 | Chen | |
| 5,945,094 A | 8/1999 | Martin et al. | |
| 5,970,643 A | 10/1999 | Gawel, Jr. | |
| 5,980,064 A | 11/1999 | Metroyanis | |
| 6,017,139 A | 1/2000 | Lederer | |
| 6,044,202 A | 3/2000 | Junkel | |
| 6,104,867 A | 8/2000 | Stathakis et al. | |
| 6,105,916 A | 8/2000 | Zlotnik et al. | |
| 6,106,786 A | 8/2000 | Akahoshi | |
| 6,143,313 A | 11/2000 | Ito et al. | |
| 6,145,241 A | 11/2000 | Okuno | |
| 6,189,327 B1 | 2/2001 | Strauss et al. | |
| 6,196,706 B1 | 3/2001 | Cutts | |
| 6,236,807 B1 | 5/2001 | Ruffolo et al. | |
| 6,241,161 B1 | 6/2001 | Corbett | |
| 6,254,065 B1 | 7/2001 | Ehrensperger et al. | |
| 6,278,840 B1 | 8/2001 | Basagañas Millan | |
| 6,285,830 B1 | 9/2001 | Basagañas Millan | |
| 6,354,710 B1 | 3/2002 | Nacouzi | |
| 6,361,752 B1 | 3/2002 | Demarest et al. | |
| 6,371,450 B1 | 4/2002 | Davis et al. | |
| 6,391,329 B1 | 5/2002 | Ito et al. | |
| 6,416,242 B1 | 7/2002 | Kaufmann | |
| 6,446,583 B2 | 9/2002 | Vieira | |
| 6,454,425 B1 | 9/2002 | Lin | |
| 6,466,739 B2 | 10/2002 | Ambrosi et al. | |
| 6,484,438 B2 | 11/2002 | Matsunaga et al. | |
| 6,536,160 B1 | 3/2003 | Morlier et al. | |
| 6,555,068 B2 | 4/2003 | Smith | |
| 6,567,613 B2 | 5/2003 | Rymer | 392/390 |
| 6,580,875 B2 | 6/2003 | Rymer | |
| 6,616,308 B2 | 9/2003 | Jensen et al. | |
| 6,619,560 B1 | 9/2003 | Chun | |
| 6,697,571 B2 | 2/2004 | Triplett et al. | |
| 6,766,817 B2 | 7/2004 | da Silva | |
| 6,775,470 B2 | 8/2004 | Zobele et al. | |
| 6,793,149 B2 | 9/2004 | Schramm | |
| 6,854,717 B2 | 2/2005 | Millan | |
| 6,862,403 B2 | 3/2005 | Pedrotti et al. | |
| 6,871,794 B2 | 3/2005 | McEwen | |
| 6,889,003 B2 | 5/2005 | Triplett et al. | |
| 6,899,280 B2 | 5/2005 | Kotary et al. | 239/34 |
| 6,909,840 B2 | 6/2005 | Harwig et al. | |
| 6,920,282 B2 | 7/2005 | He et al. | |
| 6,923,383 B1 | 8/2005 | Joshi et al. | |
| 6,931,202 B2 | 8/2005 | Pedrotti et al. | |
| 6,938,883 B2 | 9/2005 | Adams et al. | |
| 6,950,607 B2 | 9/2005 | Yip et al. | |
| 6,966,665 B2 | 11/2005 | Limburg et al. | |
| 7,007,863 B2 | 3/2006 | Kotary et al. | |
| 7,014,818 B2 | 3/2006 | Rymer | |
| 7,018,644 B2 | 3/2006 | Lang | |
| 7,032,831 B2 | 4/2006 | Duston et al. | |
| 7,244,398 B2 * | 7/2007 | Kotary et al. | 422/124 |
| 2001/0053283 A1 | 12/2001 | Levine et al. | |
| 2002/0021892 A1 | 2/2002 | Ambrosi et al. | |
| 2002/0080601 A1 | 6/2002 | Meltzer | |

| | | | | | | |
|---|---|---|---|---|---|---|
| 2002/0093834 | A1 | 7/2002 | Yu et al. | ES | 1 005 422 | 11/1988 |
| 2002/0136542 | A1 | 9/2002 | He et al. | FR | 2 483 782 | 12/1981 |
| 2002/0136886 | A1 | 9/2002 | He et al. | GB | 2 285 579 | 7/1995 |
| 2003/0005620 | A1 | 1/2003 | Ananth et al. | WO | WO 95/10352 | 4/1995 |
| 2003/0007887 | A1 | 1/2003 | Roumpos et al. | WO | WO 97/13539 | 4/1997 |
| 2003/0044326 | A1 | 3/2003 | Yamasaki et al. | WO | WO 98/19526 | 5/1998 |
| 2003/0053305 | A1 | 3/2003 | Lin | WO | WO 98/46284 | 10/1998 |
| 2003/0063902 | A1 | 4/2003 | Pedrotti et al. | WO | WO 98/58692 | 12/1998 |
| 2003/0136886 | A1 | 7/2003 | Zhu | WO | WO 01/02025 | 1/2001 |
| 2004/0065749 | A1 | 4/2004 | Kotary et al. | WO | WO 01/23008 | 4/2001 |
| 2004/0074982 | A1 | 4/2004 | Kotary et al. ........ 239/44 | WO | WO 02/30220 | 4/2002 |
| 2004/0141315 | A1 | 7/2004 | Sherburne | WO | WO 02/31413 | 4/2002 |
| 2004/0182949 | A1 | 9/2004 | Duston et al. | WO | WO 03/013618 | 2/2003 |
| 2004/0184969 | A1 | 9/2004 | Kotary et al. | WO | WO 03/028775 | 4/2003 |
| 2004/0246711 | A1 | 12/2004 | Brenchley et al. | WO | WO 03/061716 | 7/2003 |
| 2004/0257798 | A1 | 12/2004 | Hart et al. ........ 239/44 | WO | WO 03/086487 | 10/2003 |
| 2004/0262419 | A1 | 12/2004 | Kotary et al. | WO | WO 03/092750 | 11/2003 |
| 2004/0262420 | A1 | 12/2004 | Hansen et al. | WO | WO 2004/030708 | 4/2004 |
| 2004/0265189 | A1 | 12/2004 | Schwarz | | | |
| 2004/0265196 | A1 | 12/2004 | Varanasi et al. | | | |
| 2005/0053368 | A1 | 3/2005 | Pesu et al. | | | |
| 2005/0053528 | A1 | 3/2005 | Rymer ........ 422/124 | | | |
| 2005/0178345 | A1 | 8/2005 | Crapser | | | |
| 2005/0180736 | A1 | 8/2005 | Zobele | | | |
| 2005/0185392 | A1 | 8/2005 | Walter et al. | | | |

FOREIGN PATENT DOCUMENTS

| | | |
|---|---|---|
| DE | 29 907 125 U1 | 7/1999 |
| DM | 054926 | 9/2000 |
| EP | 0 882 459 | 12/1998 |
| EP | 962 132 | 12/1999 |
| EP | 1 031 446 | 8/2000 |
| EP | 1 175 833 | 1/2002 |
| EP | 1 270 021 | 1/2003 |
| EP | 1 283 062 | 2/2003 |
| EP | 1 392 368 | 10/2003 |

OTHER PUBLICATIONS

Office Action for U.S. Appl. No. 11/289,471 dated Oct. 16, 2006.
International Search Report and Written Opinion, Aug. 16, 2004, Appl. No. PCT-US04-008436.
International Search Report and Written Opinion, Aug. 16, 2004, Appl. No. PCT-US04-008437.
International Search Report and Written Opinion, dated Nov. 30, 2004, Appl. No. PCT-US2004-020586.
"INGLOW™ Candle Company" www.inglowcandle.com (2002).
"Luna Candles" http:--www.epartyunlimited.com-luna-candles.html (print date 2005).
Kotary, U.S. Appl. No. 11/341,166, filed Jan. 27, 2006.
International Search Report and Written Opinion in PCT/US04/20238 dated Dec. 1, 2004.
Office Action in U.S. Appl. No. 10/608,357 dated Sep. 5, 2008.

* cited by examiner

DISPENSING SYSTEM FOR A VOLATILE LIQUID

CROSS REFERENCE TO RELATED APPLICATIONS

This application is a continuation-in-part of U.S. patent application Ser. No. 10/608,717, filed Jun. 27, 2003, now abandoned a continuation-in-part of U.S. patent application Ser. No. 10/394,621, filed Mar. 21, 2003, now U.S. Pat. No. 7,032,831 and a continuation-in-part of U.S. patent application Ser. No. 10/607,702, filed Jun. 27, 2003 now abandoned.

BACKGROUND OF THE INVENTION

Field of the Invention

The application relates to dispensing systems for volatile liquids and, more particularly, to a dispensing system incorporating a capillary member.

BRIEF DESCRIPTION OF THE DRAWINGS

FIG. 12 is an enlarged view of FIG. 11 showing breakage of the wick in a predetermined region along the length of the wick;

DETAILED DESCRIPTION OF THE INVENTION

Figures 1, 2, 3, 4, 5, 5A:
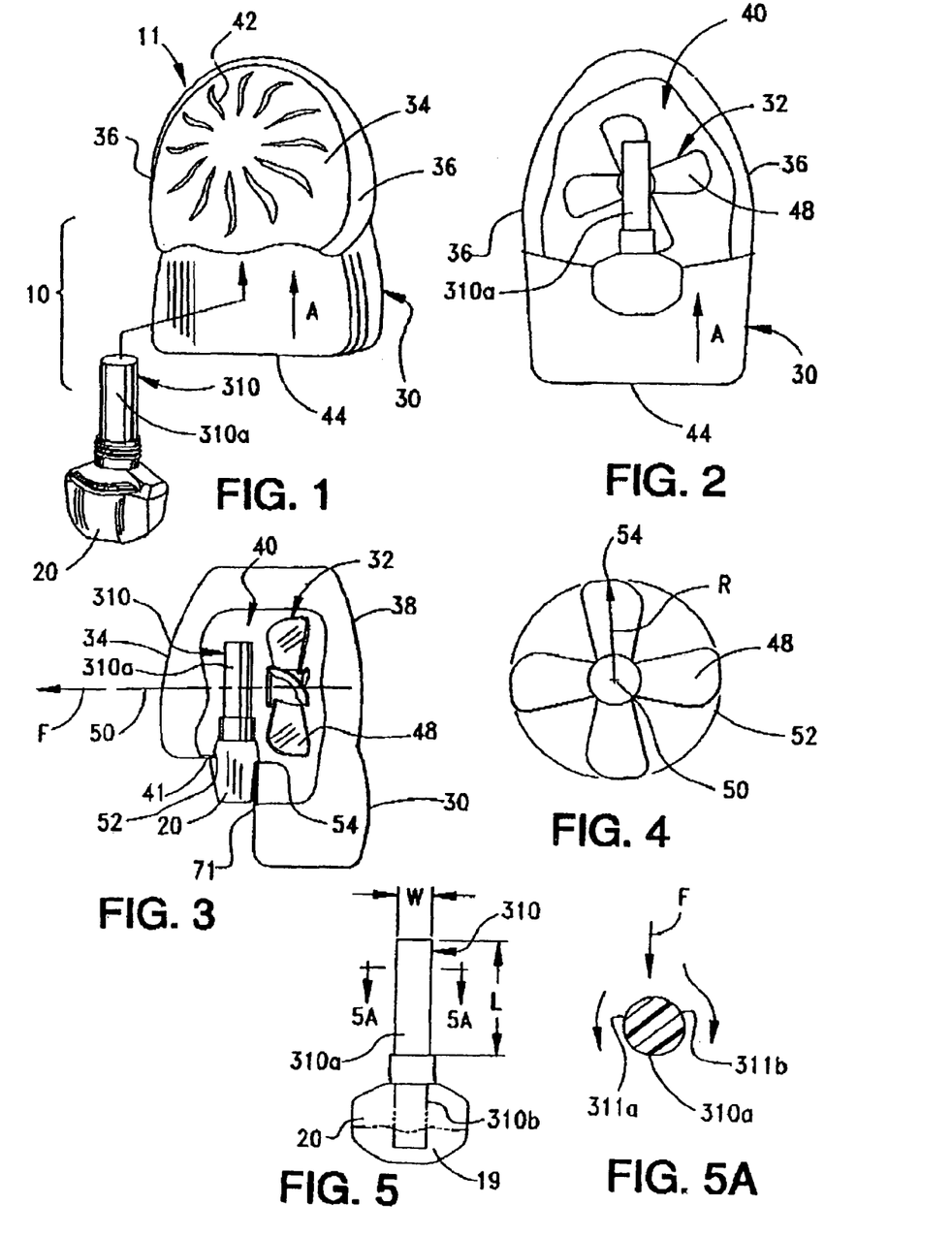
FIG. 1 is a perspective view showing insertion of a wick into a housing of a dispenser of the present invention.
FIG. 2 is a front schematic view of the dispenser of FIG. 1 showing the dispenser housing partially cut away with the wick positioned in the housing.
FIG. 3 is a side view showing the dispenser housing partially cut away with the wick positioned in the housing as shown in FIG. 2.
FIG. 4 is a front view of the fan blades.
FIG. 5 is a front schematic view of the wick secured in a container for insertion into the housing of the dispenser as shown in FIG. 1.
FIG. 5A is a cross sectional view of the wick of FIG. 5 taken along line 5A-5A transverse to a length of the wick.

Referring to FIGS. 1-3, a dispensing system 10 is designed to disseminate a volatile liquid, such as a fragrance compound, into a room. The fragrance compound is disseminated via a forced air stream flowing around a capillary member at room ambient temperature. According to the present invention, dispensing system 10 comprises a dispensing apparatus 11 including a housing 30, a motorized fan 32 mounted in housing 30 for generating an air stream, and a capillary member 310 coupled to dispensing apparatus 11.

At least a portion 310a of a body of the capillary member 310 is impervious to passage of an air stream, with the fan activated, through the body in a direction of flow F of the air stream. In the embodiment shown in FIGS. 1-3, capillary member 310 is in the form of a porous wick. Capillary member 310 may be embodied in other forms (not shown). However, for illustrative purposes, the terms "capillary member" and "wick" will be used interchangeably hereinafter.

The volatile liquid migrates along wick 310 from the reservoir or container 20 to the exterior where it is evaporated from the surface of wick 310 by forced airflow generated by a motorized fan mounted in housing 30.

Referring to FIGS. 1-3, housing 30 generally includes a front wall 34, a side 36 formed at each lateral end of front wall 34, and a rear wall 38 formed opposite front wall 34. Front wall 34, sides 36, and rear wall 38 combine to form an enclosure or interior 40 for housing fan 32 and for receiving wick 310 into the air stream generated by fan 32. One or more air inlet ports (not shown) may be formed in rear wall 38 for providing intake air for fan 32. Also, one or more air outflow ports 42 are provided in front wall 34 to provide a path for outflow of the air stream from enclosure 40. A lower portion of housing 30 forms a base 44 configured to enable dispenser 10 to rest on a flat surface. A switch or button (not shown) may be provided on an exterior surface of housing 30 to enable activation and deactivation of the fan motor.

Referring to FIGS. 3 and 4, a motor for fan 32 is powered by a battery (not shown) positioned in base 44 of housing 30. Access to the battery may be provided by a hinged or removable access plate formed in base 44. Fan 32 includes a plurality of fan blades 48 that rotate about a fan axis of rotation 50 during operation of the fan. During rotation, fan blades 48 trace out a circumferential path 52. As shown in FIG. 4, fan blades 48 each have a dimension R extending from axis of rotation 50 to an edge 54 of the respective fan blade 48 farthest from axis of rotation 50.

Power to the fan motor may be controlled by a fan motor control circuit such that the motor turns the fan according to a predetermined "on-off" cycle. Generally, the predetermined "on-off" cycle will have a motor "on" period of a predetermined length and a motor "off" period of a predetermined length. In one embodiment, the "on" and "off" ratio of predetermined length of time is approximately 1 to 3. For example, the predetermined "on" period is approximately five minutes and the predetermined "off" period is approximately fifteen minutes. The fan motor control circuit may repeat the predetermined cycle until power to the dispensing apparatus is interrupted. In addition, cycling of the fan motor may be automated using any one of a number of methods. For example, power to the fan motor may be controlled by an appropriately configured integrated circuit coupled to the fan motor.

Referring now to FIGS. 3, 5 and 5a, the portion 310a of the wick body positioned in the air stream is impervious to passage of the air stream through the body in the direction F of the air stream. The body of the wick is positioned and secured with in enclosure 40 formed by housing 30, such that the air stream passes unobstructed over opposing surfaces 311a and 311b of portion 310a aligned generally, as demonstrated by dashed line OS in FIG. 5A transverse to direction F of the air stream.

The efficiency and effectiveness of this dispenser is enhanced with the free flow of the air stream generated by fan 32 about wick portion 310a. As can be seen in FIGS. 2 and 3 capillary member portion 310a is spaced apart from any interior portion of housing 30.

Wick 310 may be secured in the desired position by coupling wick 310 to dispenser housing 30 using any one of numerous methods. In the embodiment shown in FIGS. 1-5A wick 310 is secured in a container 20 holding the volatile liquid to be dispensed. Another portion 310b of wick 310, as seen in FIG. 5, is in communication with the volatile liquid 19 in container 20. Portion 310a of wick 310 extends outside container 20 and is exposed to ambient air when fan 32 is not in operation, and is immersed in the air stream when fan 32 is in operation.

Referring to FIG. 3, dispenser housing 30 has opposing sidewalls 41 and 71. Each of opposing sidewalls 41 and 71 has a corresponding edge portion 52 and 54, respectively. Edge portions 52, 54 define an opening adapted to receive wick 310 and a portion of container 20 into enclosure 40. A retention structure is formed along one or more of opposing sides of container 20 to help position and releasably secure container 20 between opposing sidewalls 41 and 71 of housing 30. The retention structure, in this example, are molded curves or detents formed in container 20 sidewalls. When container 20 is secured to dispenser housing 30 as described above, wick 310 is positioned in the air stream generated by fan 32. As seen in FIGS. 2 and 3, when wick 310 is in its desired position within enclosure 40, the portion of the wick exposed to ambient air and to air stream when generated is spaced apart from any portion of housing 30 within the interior 40. Also, as seen in FIGS. 2 and 3, wick 310 may be positioned along the fan rotational axis 50.

Figure 6:
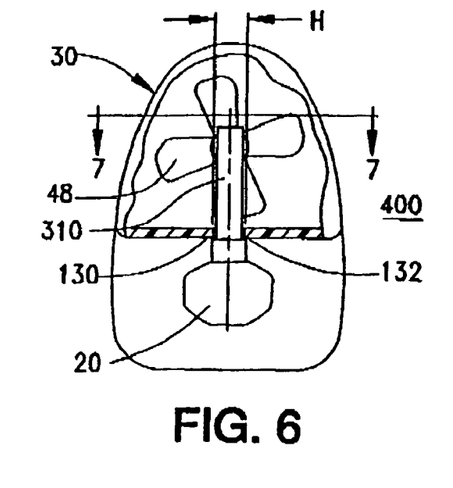
FIG. 6 is a schematic front elevational view of the dispenser of FIG. 1 showing an embodiment of the guide of the present invention.

Examples of other retention structures suitable for the purpose described above can include contact adhesives, hook loop fasteners between container 20 and housing 30, as may be employed to secure container 20 to housing 30 in FIG. 6. Other suitable retention structures could include a jam fit of container 20 into an opening in housing 30 (not shown).

Referring to FIGS. 2-5, in the present invention the size of a profile of wick 310 immersed in the air stream may be controlled relative to the size of fan 32 used to generate the air stream. To accomplish this, wick 310 is formed to have a width dimension W, as shown in FIG. 5, which does not exceed 1.2 times the dimension R (FIG. 4), extending from axis of rotation 50 (FIG. 3) to the edge 54 of any fan blade 48 farthest from axis of rotation 50. In one example, R=21.15 mm and W=12.7 mm. Width dimension W may be measured transverse to rotational axis 50 of the fan. Width dimension W may also be measured transverse to a length dimension L (FIG. 5) of wick 310. In alternative embodiments, wick 310 may be formed to have a width dimension W which does not exceed 0.80 times the dimension R, 0.60 times the dimension R, or any other desired fraction of the dimension R.

Figure 7:
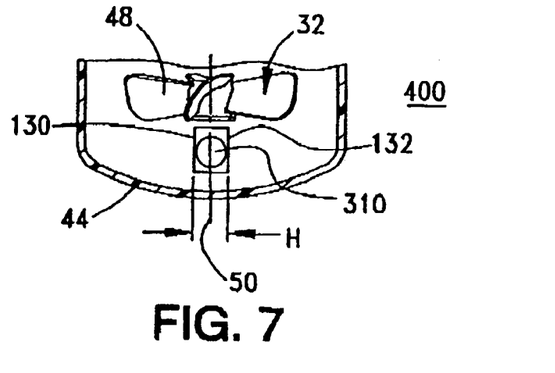
FIG. 7 is a cross-sectional view of the dispenser of FIG. 6 taken along line 7-7 of the present invention.
Figure 8:
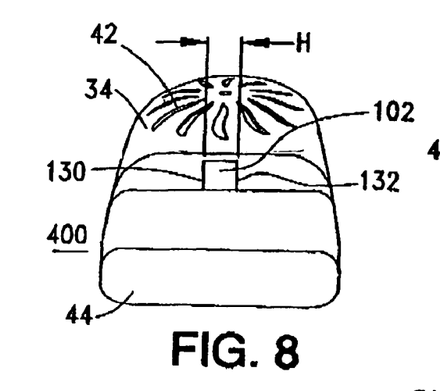
FIG. 8 is a bottom perspective view of the embodiment of the dispenser of the present invention of FIG. 6 without the container and wick.

Referring now to FIGS. 6, 7 and 8, a guide, generally designated 400, may be associated with housing 30 to define an opening 102 having a predetermined dimension H to selectively receive wick 310 therein. In the embodiment shown in FIGS. 6, 7 and 8, guide 400 comprises a pair of opposing sidewalls 130 and 132 formed in housing 30 and defining opening 102 into an interior portion of housing 30. In this embodiment, predetermined dimension H, as seen in FIG. 7, is defined by the spacing between sidewalls 130 and 132. As seen in FIGS. 7 and 8, predetermined dimension H of opening 102 may be oriented generally transverse to fan axis of rotation 50. Guide 400 is positioned in association with housing 30 such that when wick 310 is selectively received in opening 102, guide 400 effectively positions the portion 310a of the wick body which is impervious to passage of the air stream through the body of the wick in the direction of air stream F, such that the air stream passes unobstructed over opposing surfaces 311a and 311b of portion 310a aligned generally transverse to a direction F of the air stream as well as axis of rotation 50 of fan 32. Generally, guide 400 may either be formed integral with housing 30 or formed as one or more separate components which are then coupled to housing 30 and positioned in the interior 40 or exterior of housing 30.

Figure 9:
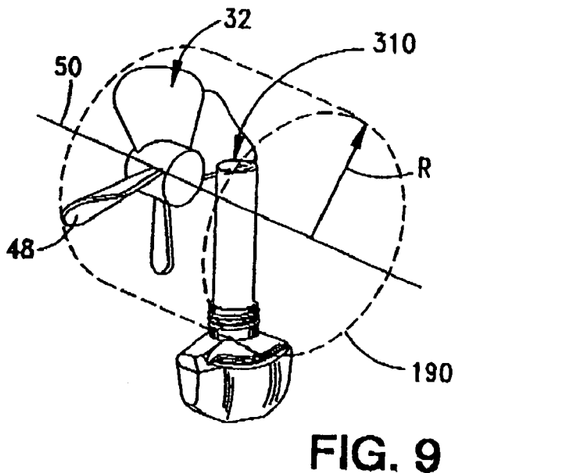
FIG. 9 is a schematic perspective view showing the positioning of the wick in a cylindrical volume defined by the fan mounted in the dispenser housing.

As described herein, wick 310 is to be inserted into housing opening 102 in a direction indicated by arrow "A", (FIGS. 1 and 2). Referring to FIGS. 4 and 9, for purposes of positioning wick 310 in the air stream generated by fan 32 as described above, a cylindrical volume 190 is defined which is centered along fan axis of rotation 50 and which has a radius R that extends from axis of rotation 50 to an edge 54 of the fan blade farthest from fan rotational axis 50. During rotation, fan blades 48 trace out a circumferential path 52. As shown in FIG. 4, fan blades 48 each have a dimension R extending from axis of rotation 50 to an edge 54 of the respective fan blade 48 farthest from axis of rotation 50. As it is desired for wick 310 to be positioned in the air stream generated by fan 32, any embodiment of a guide will generally receive wick 310 therein and position at least a portion of wick 310 within cylindrical volume 190 and if desired in a generally transverse alignment with fan rotational axis 50.

Referring to FIGS. 4-8, wick 310 may be selectively received in opening 102 based on a dimension of the wick relative to predetermined dimension H of opening 102. That is, the relationship between dimension H between and a corresponding dimension W of wick 310 may be specified so as to limit the dimension W of a wick which can be placed into the air stream of the fan.

Figure 10:
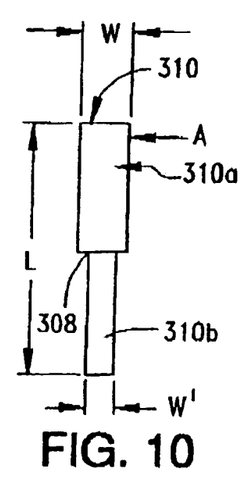
FIG. 10 is a side elevational view of an embodiment of the wick.

In general, predetermined dimension H of opening 102, as shown in FIG. 8, will be greater than a corresponding dimension W of wick 310, as shown in FIG. 10. In addition, predetermined dimension H may be defined with respect to a dimension of fan 32. For example, referring to FIGS. 4 and 8, where a blade 48 of fan has a length R measured from fan axis of rotation 50 to the edge 54 of the fan blade farthest away from the axis, predetermined dimension H is defined so as not to exceed 1.25 R. In alternative embodiments, predetermined dimension H may be defined so as not to exceed 1.1 R, 0.9R, or any other pre-determined lesser multiple of R. Wick dimension W may be correspondingly defined with respect to fan blade dimension R such that a slight clearance fit is provided between wick 310 and portions of guide defining opening 102. For example, when predetermined dimension H is defined so as to not exceed 1.25R, wick dimension W may be defined so as to not exceed 1.2 R.

Forces acting on wick 310 (e.g., during handling of the wick by a user) may be sufficient to cause breakage of the wick. For example, referring to FIGS. 10 and 11, if the portion 310a of wick 310 exposed to ambient air is subjected to a force acting in a direction indicated by arrow "A" while the portion of wick 310 resides inside container 20 is prevented from moving, the applied force may be sufficient to cause breakage of wick 310. In such a case, it is desirable that the portion of wick 310 in contact with container 20 remains secured in the container after breakage of wick 310 in order to prevent leakage of volatile liquid from container 20 through the container opening. To ensure that a portion of wick 310 remains in and blocking the container opening after wick breakage, it is desirable to ensure that wick 310 breaks at a predetermined point along the length of the wick. To help ensure wick breakage at a predetermined location on wick 310 when a force "A" is applied to the wick, one or more breakage features may be incorporated into the structure of wick 310 which act to facilitate breakage of wick 310.

Figure 11:
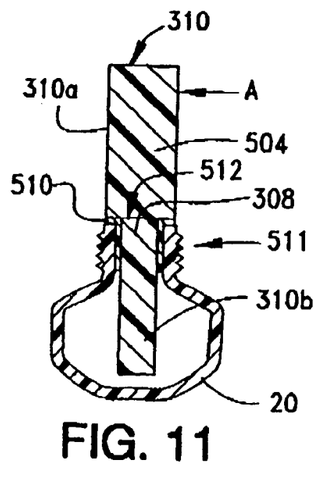
FIG. 11 is an enlarged cross-sectional view taken along a longitudinal axis showing the wick of FIG. 10 secured to a container for holding a volatile liquid.

As seen in FIG. 11, wick 310 may be secured in retention member or annular plug 510 of container 20 such that a location along wick 310 at which breakage is to occur is positioned proximate retention member opening 511 or container opening 512. This enables retention member 510 or container 20 to act as a pivot about which an exposed portion of wick 310 may rotate during brakeage, as shown in FIG. 12.

Referring to FIG. 11, in one embodiment of wick 310, the discontinuity is formed by a junction 308 between portion 310a, as seen in FIG. 10, of wick 310 and another, adjacent portion 310b of wick 310 having a different cross sectional area than portion 310a. Wick 310 has one or more thickness dimensions measured in a direction generally transverse to a length dimension L of wick 310. Generally, each thickness dimension will be smaller than length L. The embodiment of wick 310 shown in FIG. 10 has multiple thickness dimensions W, W'. In a particular version of this embodiment, wick 310 has a cylindrical shape and portion 310b of wick 310 has a diameter different from portion 310a of wick 310. Other types of discontinuities (not shown) may incorporated into the wick structure alternatively (or in addition to) the cross-sectional area change described above.

Referring again to FIGS. 10 and 11, when wick 310 is mounted in container 20, the wick will generally be secured in either a retention member 510 or directly in container 20, such that a breakage feature incorporated into the wick resides proximate an end portion of retention member 510 or an end portion of container 20. For example, as seen in FIG. 11, wick 310 of FIG. 12 is secured in retention member 510 mounted in container opening 512 of container 20.

Referring to FIG. 10, Wick 310 may be secured in retention member opening 511 using an interference fit, adhesive or any one of several other known methods. Any method used to secure wick 310 in retention member opening 511 should aid in preventing leakage of the volatile liquid along a path extending between wick 310 and retention member 510. Similarly, retention member 510 may be secured in container opening 512 using an interference fit, adhesive or the like. Any method used to secure retention member 510 within container opening 512 should aid in preventing leakage of the volatile liquid along a path extending between retention member 510 and container 20.

Also, as seen in FIG. 10, portion 310a of wick 310 residing on a first side of junction 308 will generally be positioned outside container 20, while another portion 310b of wick 310 residing on an opposite side of the discontinuity will be positioned inside container 20. In this manner, as described above, positioning of the discontinuity in relation to container 20 provides some predictability as to the location of a breaking point of wick 310 with respect to container 20 when force "A" is applied to wick 310.

FIGS. 10 and 12 show the general manner in which the breakage feature operates. Referring to FIG. 10, when a force is applied to wick 310 (for example, in the direction indicated by arrow "A"), tensile and compressive stresses are generated in the wick material. As seen in FIG. 12, when another portion 310b of wick 310 is secured within container 20 while a force in a direction indicated by arrow "A" is applied to portion 310a of wick 310 exposed to ambient air, a region of relatively high stresses will be created at junction 308 between the adjacent wick portions, due to the relatively abrupt change in cross-sectional area between the adjacent portions. If a sufficient force is applied to the exposed wick portion wick portion 310a, wick 310 will tend to break along junction 308 with retention member or container 20 acting as a pivot, about which exposed wick portion may rotate.

Referring to FIG. 11, container 20 may include a small hole (e.g., a vent-hole) (not shown) formed near the container opening 512 to help counter the effects of a vacuum that can form in the head-space of the container 20. As stated previously, wick 310 transports the liquid to the surface of the upper portion 504 of wick 310 by a principle called capillary action. In particular, the wick material contains pores which are interconnected with openings within the wick. These interconnected pores act as capillaries, which cause the liquid to be drawn into them. As the liquid is drawn from the container and transported up the porous wick 310, a vacuum is created in the head-space of the container 20. The formation of a vacuum in the head-space of the container 20 decreases the rate that the liquid is wicked from the reservoir to the surface. This decrease in the wicking rate translates directly into a decrease in the release rate of the liquid to the ambient air. Accordingly, in order to combat the formation of the vacuum in the head-space, it is often preferable to form a vent-hole in the vicinity of the head-space of the container 20. However, if the container 20 is overturned, either during shipping or, later, during handling of the bottle by the consumer, it is possible for the concentrated liquid in the container 20 to leak out of the vent-hole. Therefore, if is preferable to design a device that does not require a vent-hole.

It has been found that if the pore size of the wick 310 is below a critical size, the vent-hole can be eliminated without sacrificing the release rate of the vaporizable liquid into the ambient air. Because the capillary force increases as the pore size of the wick 310 decreases, a wick 310 with very small porosity has a very strong capillary force. This strong capillary force allows the wick 310 to continue to be able to transport the liquid from the container 20 to the surface of the wick 310 even though a vacuum has formed in the head-space of the container 20. In other words, a wick 310 with a very small pore size is able to overcome the vacuum effect that is present in the head-space of the container 20.

The critical size of the wick 310 is determined by the surface tension of the liquid, the compatibility of the wick 310 and liquid (i.e., the contact angle), and the extent to which a vacuum is generated with the head-space of the container 20. In particular, it has been found that if wick 310 is manufactured with a mean pore size that is below about four microns, the effects of a vacuum in the head-space of the container 20 can be greatly decreased. Specifically, it has been found that it is most preferable that the mean pore size of wick 310 be below about one micron. When the wick 310 has a mean pore size of below four microns, and preferably below one micron, it has been found that the wick 310 is still able to effectively function to transport the liquid from the container 20 to the surface of the wick 310.

When using a device of this invention, it is not necessary to provide a vent-hole in the upper part of the container 20 because the vacuum effects are substantially decreased. By eliminating the vent-hole, the problem of spillage or leakage that occurs as a result of the existence of the vent-hole is also eliminated.

The mean pore size of the wick 310 can be determined by any standard test for determining porosity and pore size distribution. For example, mercury porosimetry is a method that gives information on porosity and pore size distribution for rigid wicks. It is based on the measurement of differential increments in the amount of mercury intruded into the wick 310 as a function of increasing applied pressure.

It has also been found that another advantage in using a wick 310 with a mean porosity of below about four microns, and preferably below about one micron, is that the lower porosity decreases the likelihood of the liquid spilling or leaking through the wick 310 itself. Since the upper portion 310a of wick 310 is exposed to the ambient air, if the container 20 is overturned, it is possible for liquid to leak out through a wick of conventional pore sizes. Using a smaller porosity wick 310 of this invention, however, decreases the ability of the liquid to travel through the wick 310 when the container 20 is overturned. The above-described benefits of using a wick 310 with a mean pore size of below about four microns, and preferably below about one micron, can be obtained with wicks of many different shapes.

Wick 310 can be made of a variety of materials. It is preferable that the wick 310 be rigid enough to provide minimal contact area with the surface it may contact. Polymeric wicks, for example, have been found to be effective for these purposes. In particular, wicks composed of ultra high molecular weight, high density polyethylene (HDPE) have been found to be suitable. Such wicks are generally comprised of blends of HDPE in particle form, and the blends are developed to meet the target pore characteristics of the wick 310.

Preferably, the solubility parameter of the polymer used in wick 310 is significantly different from that of any of the components contained in the liquid. This prevents wick 310 from swelling (or other changes) that may lead to a change in the pore size and porosity of the wick 310, which would consequently affect the release rate of the vaporizable liquid into the ambient air.

Figure 13:
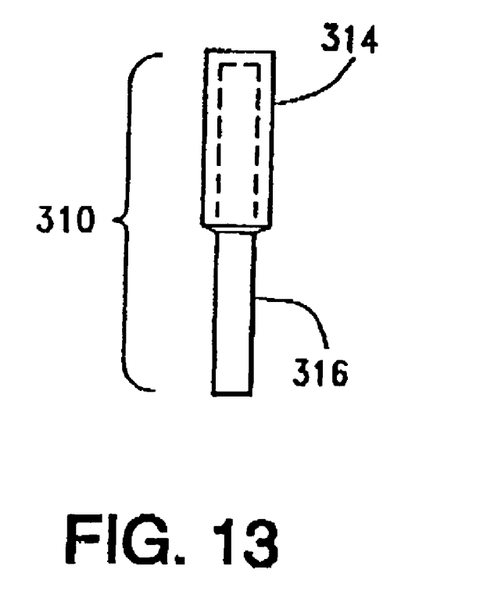
FIG. 13 is a side elevational view of another embodiment of the wick.

As shown in FIG. 13, it is also possible to provide a wick 310 with an outer layer 314 that is made up of a material with larger pore sizes. The large pore outer section 314 completely surrounds the exposed portion of the wick. The small pore size section 316 extends into the container 20 and is in contact with the liquid. In this manner, the smaller pores of the inner portion 316 of the wick 310 allow the delivery system to be constructed without a vent-hole, while the larger pores of the outer portion 314 provide a maximum release rate of the vaporizable liquid off the surface of the wick 310 that is exposed to the ambient air. It should be noted, however, that the large pore section 314 need not completely surround the upper region of the small pore section 316 as shown in FIG. 13 in order to provide the benefits of this invention.

It is often desired that the volatile liquid dispenser described herein exhibit an initial spike in the release rate of the volatile liquid when the device is first activated. For example, when a fragrance dispensing device is activated, an initial spike in the release rate of the volatile liquid fragrance compound is desired in order to quickly disperse into the air a sufficient amount of the fragrance compound, for example, to effectively enhance the aroma of the surrounding area. Once an optimum level of fragrance compound is present in the ambient air of the operating area, however, the release rate of the fragrance compound should be decreased to an amount that is sufficient to maintain that optimum level. By having two sections of varying pore size exposed to the ambient air at the same time, it is possible to achieve an initial spike effect.

Figure 13A:
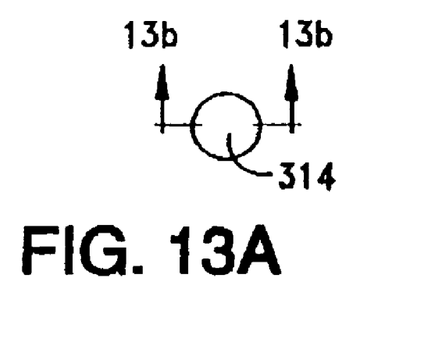
FIG. 13A is a top view of the wick of FIG. 13.
Figure 13B:
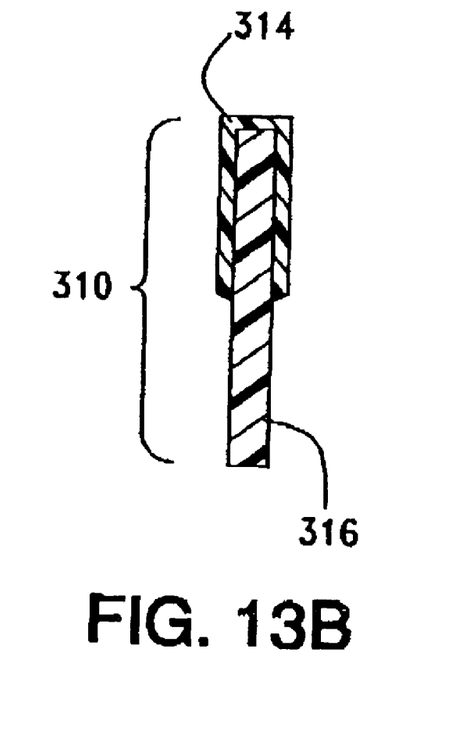
FIG. 13B is a cross-sectional view of the wick of FIG. 13A taken along line 13b-13b in FIG. 13A.

Referring to FIGS. 13A and 13B, the first section 314 has a predetermined larger pore size than the second section 316. In this embodiment it is desirable to have a ratio of 2 to 1 for the pore size section of 314 to section 316. Both sections of the wick are positioned into the ambient air.

INDUSTRIAL APPLICABILITY

The present invention provides a dispensing system for a volatile liquid incorporating a capillary member. A portion of the capillary member is positioned within an air stream generated by a fan. Flow of the air stream over the capillary member causes evaporation of volatile liquid from an external surface of the capillary member. The portion of the capillary member positioned in the air stream is impervious to passage of the air stream through the capillary member in a direction of the air stream. This portion of the capillary member is positioned within the air stream such that the air stream passes unobstructed over opposing surfaces of the capillary member aligned generally transverse to the direction of the air stream. This positioning of the capillary member in relation to the fan ensures efficient flow of air over the capillary member, thereby ensuring rapid and efficient dissemination of the volatile liquid flowing through the capillary member.

It should be understood that the preceding is merely a detailed description of various embodiments of this invention and that numerous changes to the disclosed embodiment can be made in accordance with the disclosure herein without departing from the spirit or scope of the invention. The preceding description, therefore, is not meant to limit the scope of the invention. Rather, the scope of the invention is to be determined only by the appended claims and their equivalents.

I claim:

1. A dispensing system for a volatile liquid, comprising:

a fan adapted to push an air stream;

a capillary member that is in fluid communication with a reservoir for the volatile liquid, the capillary member having a body, in which a portion of the body is positioned within the air stream with the fan activated; in which the portion of the body is impervious to passage of the air stream therethrough in a direction of the air stream and in which the air stream passes unobstructed over opposing surfaces of the capillary member aligned generally transverse to the direction of the air stream; and a guide associated with the fan and defining opening, having a predetermined dimension, to selectively receive the capillary member and to position the portion of the body such that the portion of the body is in the air stream when the fan is activated;

wherein a blade of the fan has a dimension R extending from an axis of rotation of the fan blade to an edge of the fan blade farthest from the axis of rotation; and the portion of the body of the capillary member in which the body of the capillary member has a width W which does not exceed 1.2 R.

2. The dispensing system of claim 1 in which the dispensing system includes a housing in which the portion of the body and the motorized fan are positioned within an enclosure of the housing.

3. The dispensing system of claim 1, wherein the dispensing system includes a housing to which the fan is mounted and the guide comprises opposing sidewalls defining an opening in the housing.

4. The dispensing system of claim 1, wherein a fan blade of the fan has a length R measured from an axis of rotation of the fan to the farthest end of the fan blade away from the axis of rotation and wherein the predetermined dimension of the opening does not exceed 1.25 R.

5. The dispenser of claim 1, wherein the guide is adapted to position the capillary member within a cylindrical volume centered along an axis of rotation of the fan and having a radius which extends from the axis of rotation to the farthest extension of a fan blade of the fan.

6. The dispensing system of claim 1, wherein the capillary member includes a first section formed using a material with a predetermined pore size and a second section formed using a material with a predetermined pore size that is different from that of the material of the first section.

7. The dispensing system of claim 6, wherein the ratio of the pore size of the second section to that of the first section is greater than about two.

8. The dispensing system of claim 1, wherein the dispensing system is not heated above ambient room temperature.

9. The dispensing system of claim 1, wherein a motor for the fan turns the fan according to a predetermined cycle when power is supplied to the motor, the cycle comprising a motor "on" period of a predetermined length of time and a motor "off" period of a predetermined length of time.

10. The dispensing system of claim 9, wherein the ratio of predetermined period of length of time of the motor being "on" to the predetermined length of time of the motor being "off" is approximately 1 to 3.

11. The dispensing system of claim 1, wherein another portion of the capillary member is positioned inside a reservoir containing the volatile liquid.

12. The dispensing system of claim 1, wherein the air stream is substantially cylindrical and disposed on a blowing side of the fan.

13. The dispensing system of claim 1, wherein the capillary member is substantially rigid.

14. A dispensing system for a volatile liquid, comprising:
a fan adapted to generate an air stream; and
a capillary member that is in fluid communication with a reservoir for the volatile liquid, the capillary member having a body, in which a portion of the body is positioned within the air stream with the fan activated; in which the portion of the body is impervious to passage of the air stream therethrough in a direction of the air stream and in which the air stream passes unobstructed over opposing surfaces of the capillary member aligned generally transverse to the direction of the air stream, wherein the capillary member has an external surface and a discontinuity in the surface providing a location in the capillary member having less resistance to a force applied to the capillary member than a location adjacent to the discontinuity.

15. The dispensing system of claim 14, wherein the discontinuity is formed by a junction between the portion of the capillary member and another portion of the capillary member adjacent the portion of the capillary member having a different cross sectional area than the portion of the capillary member.

16. A dispensing system for a volatile liquid, comprising:
a dispenser having a housing defining an interior;
a fan coupled with the housing and adapted to generate an air stream flowing from the fan;
a capillary member in fluid communication with a reservoir for the volatile liquid, the capillary member having a portion positioned to be immersed in the air stream in which the portion of the capillary member is spaced apart from any interior portion of the housing; and
a guide associated with the housing and defining an opening having a predetermined dimension to selectively receive the capillary member and to position the portion of the capillary member such that the portion is in the air stream when the fan is activated;
wherein the portion is positioned generally transverse to an axis of rotation of the fan.

17. The dispensing system of claim 16, wherein the portion of the capillary member is positioned within a cylindrical volume centered along an axis of rotation of the fan and having a radius which extends from the axis of rotation to the farthest extension of a fan blade of the fan.

18. The dispensing system of claim 16, wherein the dispensing system is not heated above ambient room temperature.

19. The dispensing system of claim 16, wherein the capillary member is mounted in the reservoir.

* * * * *